United States Patent [19]

Benaron

[11] Patent Number: 5,337,745
[45] Date of Patent: Aug. 16, 1994

[54] DEVICE AND METHOD FOR IN VIVO QUALITATIVE OR QUANTATIVE MEASUREMENT OF BLOOD CHROMOPHORE CONCENTRATION USING BLOOD PULSE SPECTROPHOTOMETRY

[76] Inventor: David A. Benaron, 454 Birch St., Redwood City, Calif. 94062-1031

[21] Appl. No.: 152,913

[22] Filed: Nov. 12, 1993

Related U.S. Application Data

[63] Continuation of Ser. No. 849,152.

[51] Int. Cl.$^5$ .............................................. A61B 5/00
[52] U.S. Cl. .................................. 128/633; 128/664; 128/665; 356/39
[58] Field of Search .............................. 128/633–634, 128/664–666; 356/39–41

[56] References Cited

U.S. PATENT DOCUMENTS

| | | | |
|---|---|---|---|
| 4,281,645 | 8/1981 | Jöbsis | 128/633 |
| 4,357,105 | 11/1982 | Loretz | 356/40 |
| 4,653,498 | 3/1987 | New, Jr. et al. | 128/633 |
| 4,655,225 | 4/1987 | Dähne et al. | 128/633 |
| 4,714,080 | 12/1987 | Edgar, Jr. et al. | 128/633 |
| 4,810,090 | 3/1989 | Boucher et al. | 356/39 |
| 4,882,492 | 11/1989 | Schlager | 250/346 |
| 4,927,264 | 5/1990 | Shiga et al. | 356/41 |
| 4,948,248 | 8/1990 | Lehman | 356/40 |
| 4,997,769 | 3/1991 | Lundsgaard | 436/66 |
| 5,009,230 | 4/1991 | Hutchinson | 128/633 |
| 5,078,136 | 1/1992 | Stone et al. | 128/633 |
| 5,178,141 | 1/1993 | Kanda | 128/633 |
| 5,183,042 | 2/1993 | Harjunmaa et al. | 128/633 |

Primary Examiner—Angela D. Sykes
Attorney, Agent, or Firm—Flehr, Hohbach, Test, Albritton & Herbert

[57] ABSTRACT

An improved spectrophotometer which noninvasively and qualitatively or quantitatively determines the concentration of light and other radiation absorbing substances in the bloodstream inside a radiation scattering body by assessing, at one or more wavelengths, the pulsatile changes which occur with each heartbeat in the absorbance of radiation passing through the medium, whereby the measurement is confined to the blood-stream and the absorbance of material outside of the bloodstream is cancels out. A light emitter (11), consisting of one or more radiation sources (11a, 11b, . . . 11n), emits light into a tissue sample (14) in vivo. Radiation returning to a detector (17) is filtered (21) to remove any nonpulsatile component, amplified (27), demodulated (31) to separate the component of absorbance due to each radiation source. Peak signal intensity is determined (33), and these peak signal values are stored in an absorbance register (37). Solving a matrix of n equations with n unknowns (42) yields the relative absorbance of up to n components in the bloodstream, which are stored in qualitative register (47). Correcting relative concentration (49) using the numbers stored as conversion factors (53) yields the concentration of up to n chromophores, which are stored in quantitative register (51) and displayed on an output device (55).

20 Claims, 3 Drawing Sheets

DEVICE AND METHOD FOR IN VIVO QUALITATIVE OR QUANTATIVE MEASUREMENT OF BLOOD CHROMOPHORE CONCENTRATION USING BLOOD PULSE SPECTROPHOTOMETRY

This is a continuation of application Ser. No. 07/849,152 filed on Mar. 10, 1992, now abandoned.

FIELD OF THE INVENTION

This invention relates on an in vivo blood constituent measuring device and method, and more particularly relates to a noninvasive spectrophotometer and method of measuring either the qualitative or quantitative concentration of one or more chromophores in the blood, such as bilirubin or glucose, in a medically useful fashion.

BACKGROUND OF THE INVENTION

Measuring the concentration of colored substances, called chromophores, inside the human body is of central importance in the medical management of patients, whether in the hospital or at home. Various spectrophotometric devices and methods exist in the art to measure such substances, but all have limitations that make them difficult to use when attempting to measure the bloodstream concentration of a chromophore in vivo.

The majority of spectrophotometric methods are based upon changes in the absorbance of light that occur when the amount of a chromophore encountered by light between emission and detection varies. Outside of the body, changes in the concentration of blood chromophores can be easily estimated using Beer's Law, solved for concentration as:

$$C = A/\epsilon L, \quad (1)$$

where C is the concentration, A is the absorbance of light, $\epsilon$ is a known chemical constant called the extinction coefficient, and L is the distance the light must travel through the blood. Loretz (U.S. Pat. No. 4,357,105) explicitly solves Beer's Law to teach the use of a portable device measuring the hemoglobin concentration in a blood sample placed upon slide, while Lundsgaard (U.S. Pat. No. 4,997,769) and Boucher et al. (U.S. Pat. No. 4,810,090) teach devices and methods for measuring multiple blood components based upon Beer's Law, but only when the blood is removed from the body, and is either flowing through on optical chamber or placed upon a slide.

One likely reason that many have resorted to measurement of blood outside of the body is that Beer's Law fails to work well when applied to blood in vivo. In the body, there are multiple substances that both scatter and absorb light, including bones, hair, and skin pigments, among others. Using multiple wavelengths, it is possible account for some of the absorbance, due to the skin, hair, and other substances, such as is taught by Dähne and Gross (U.S. Pat. No. 4,655,225), but accuracy is often poor. More importantly, simply measuring the total absorbance of light by a body part does not account for the fact that the concentration of many body components is different in the blood than inside tissue cells or in body structures such as bones. Glucose, for example, is often present in higher concentrations in the bloodstream than in tissue cells. This problem is completely ignored by Dähne and Gross, and also by Schlager (U.S. Pat. No. 4,882,492) who teaches a method that allows the measurement of body glucose concentration. thus, the first two essential features of a medically useful spectrophotometer not found in the current art are: 1) that it measure accurately through human tissue in vivo, and 2) that it measure the concentration in the blood, and not simply the total concentration in the body.

One method used to study blood in the body is taught by New, Jr. (U.S. Pat. No. 4,653,498) and others. It was first discovered in Japan in the early 1970's that when light is shined through a finger, there is a slowly-varying (DC) component due to absorbance by the skin, bone, finger, and blood in the veins, as well as a rapidly varying, pulsatile (AC) component that represents the swelling of the tissues with arterial blood during each heartbeat. Subtraction of the DC component from the total absorbance leaves the pulsatile AC signal wave due solely to changes in the volume of arterial blood in the tissue between light emitter and detector. Unfortunately, using this approach, Beer's Law cannot be solved quantitatively as the path length traveled by the light is unknown, and therefore L in Beer's Law remains unknown.

In order to overcome this limitation of an unknown path length, New, Jr. (U.S. Pat. No. 4,653,498), Lehman (U.S. Pat. No. 4,948,248), and others have taught a method of measuring the two types of hemoglobin (the red hemoglobin with oxygen and the blue hemoglobin without oxygen), and taking a ratio of the two absorbances. In this approach, even though L is unknown, L cancels out in the ratio to yield a unitless percentage of hemoglobin in the arteries that is carrying oxygen. This approach has even been modified by Shiga and Suzaki (U.S. Pat. No. 4,927,264) to measure the percentage of hemoglobin in the veins that is carrying oxygen. Unfortunately, when measuring glucose or bilirubin, there are no ratio of two forms of each molecule that are to be measured. Rather, what is important is the concentration of the substance in the bloodstream, a measurement that pulse oximetry inherently cannot make. There are no current devices in the art that can measure an actual blood concentration (as opposed to tissue concentration or unitless percentage ratios of concentration) of glucose, bilirubin, carbon dioxide, or other important components in vivo. Thus, a third essential feature of a medically useful spectrophotometer is: 3) that it measure a concentration (or a concentration based result such as pH, which is a logarithm of concentration in mmol/L), and not simply a unitless percentage or ratio.

Currently, many infants born in this country undergo painful, potentially harmful, blood testing because there is no optical method to effectively determine the concentration in their blood of bilirubin, the pigment responsible for jaundice. As another example, both infants and adults undergo daily, or many times a day, blood testing for blood sugar levels, and could benefit from an optical test method. Other components that could be optically tested include, but are not limited to, hemoglobin, bilirubin, glucose, ketones, cholesterol, water, medications, toxins, products of human metabolism, pH sensitive dyes, and pH sensitive blood components. What is needed, and not available in the current art, is a device that qualitatively measures almost any colored blood component, and that can make quantitative measurements upon which medical decisions can be based.

SUMMARY OF THE INVENTION

The present invention relates to a spectrophotometer that noninvasively determines the in vivo concentration of one or more of a wide array of blood chromophores by assessing, using blood pulse spectrophotometry, the pulsatile changes in absorbance between a light emitter and detector of that colored blood component. Furthermore, by comparing to a standard, such as the concentration of water, a known concentration of an injected substance, or a calibration measurement using a standard test, the device and method allow calculation of the bloodstream concentration of those substances.

OBJECTS AND ADVANTAGES

The instant invention has many significant advantages over the prior art. First, by using blood pulse spectrophotometry, only the blood concentration of these components are measured. Second, the device may be standardized on a particular person to allow a quantitative measurement of blood components such as glucose. Third, by incorporating a second measurement of a reference value with a known blood concentration, relative changes may be translated into true concentrations.

The device may yield life saving and cost saving benefits. The invention provides numerous improvements and advantages over those devices found in the prior art, or to my knowledge, are currently undergoing development. The device would provide guidelines for treatment, yet require relatively little training or skill to operate. Furthermore, the device would be portable to allow measurement of substances, such as glucose, at home.

These and other advantages will become apparent when viewed in light of the accompanying drawings and detailed description.

DESCRIPTION OF A PREFERRED EMBODIMENT

Figure 1:
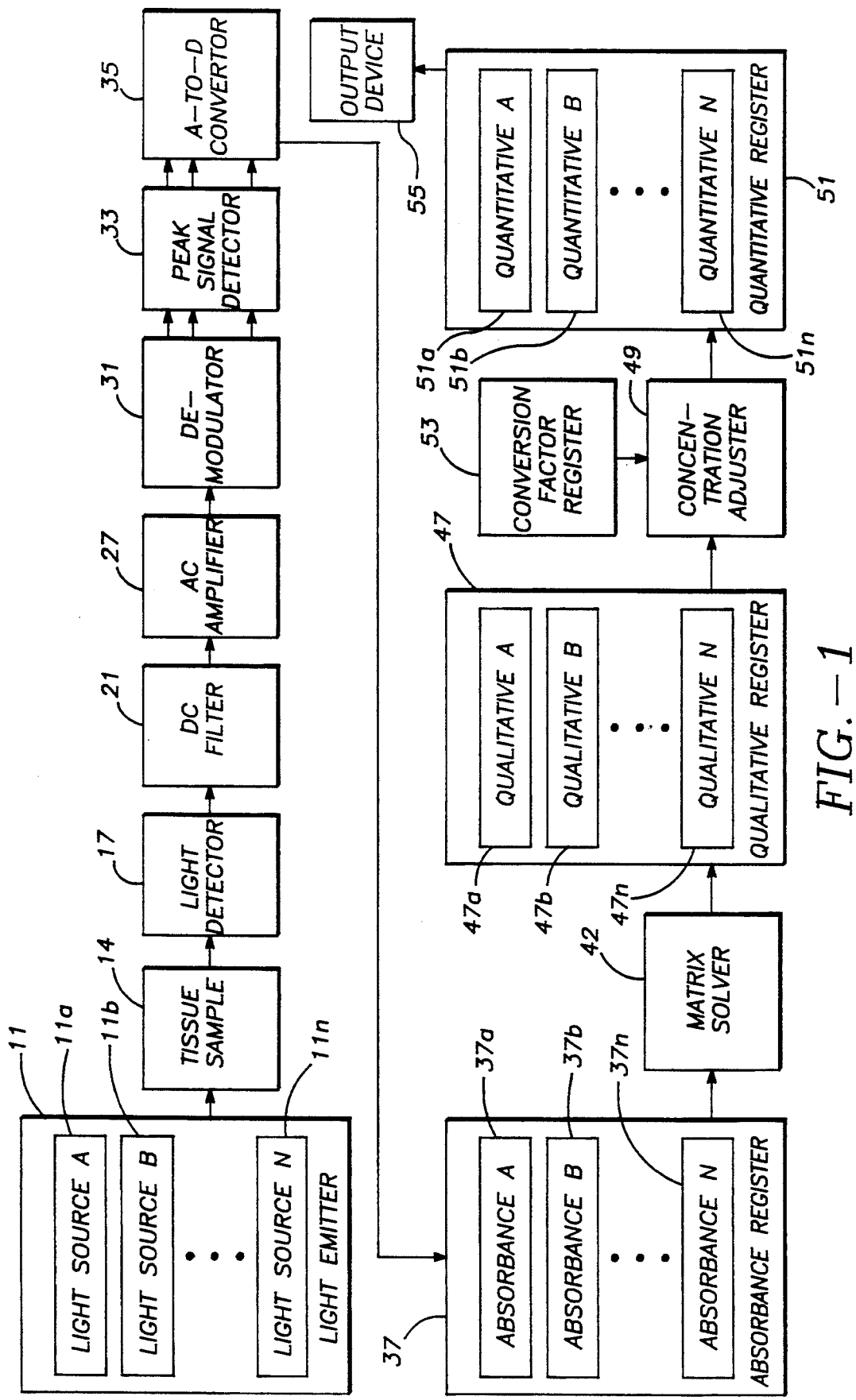
FIG. 1 is a schematic diagram of a preferred embodiment.
Figure 2A:
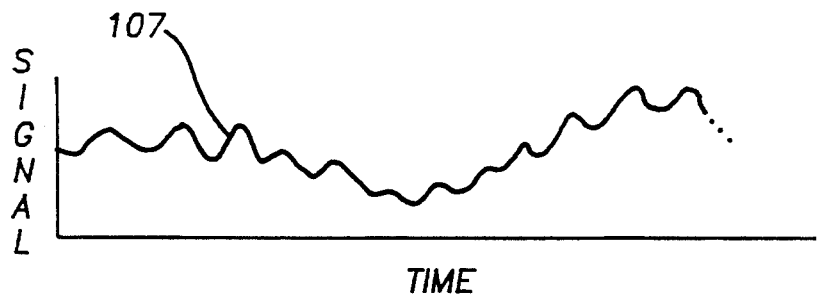
FIGS. 2A-2D show typical analog waveform diagrams from the device in operation; and, FIG. 3 shows typical intermediate numeric values from the device in operation.
Figure 2B:
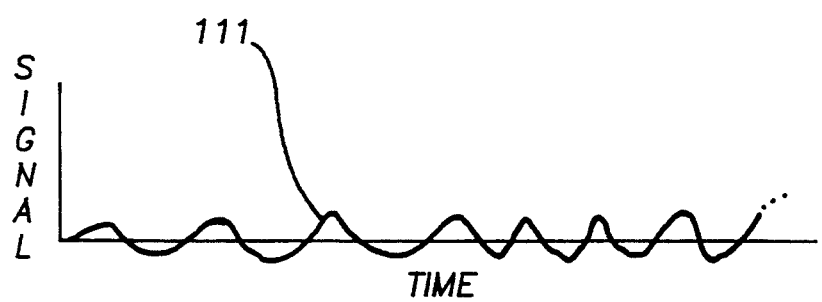
Figure 2C:
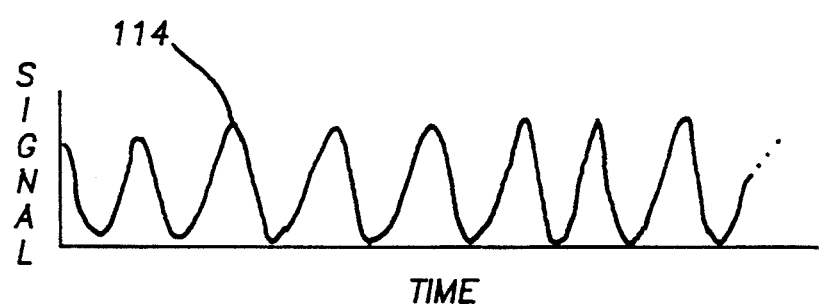
Figure 2D:
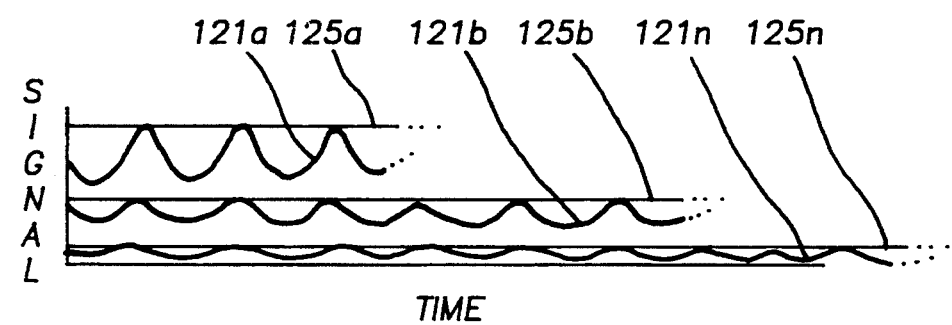

One embodiment of the improved spectrophotometer is schematically shown in FIG. 1. Here, light emitter 11 emits modulated light of one or more wavelengths of light (emitted by n light sources 11a, 11b, ... 11n) into tissue sample 14, and some of the light escaping from the sample is detected by light detector 17. The output of detector 17 is filtered to remove the invariant or slowly-varying light signal by DC filter 21, and then amplified by AC amplifier 27. As the light from emitter 11 is modulated, demodulator 31 is able to separate the AC signals from each light source into separate channels. Alternatively, light source 11 may be constructed as to emit a variable spectrum, such that a continuous range of spectra, or portions of ranges of spectra, may be emitted over time. Also, detector 17 could be configured so as to be responsive to changes in the scatter, transmission, turbidity, coherence, optical rotation, or other pulsatile parameters of the medium, so that, for example, a measurement of scattering, rather than of absorbance, may be made and separated by wavelength by demodulator 31.

The peak output for each signal from demodulator 31 is detected by peak signal detector 33, and fed into A-to-D convertor 35. Peak signals from each wavelength are stored in absorbance registers 37 (consisting of n registers 37a, 37b, ... 37n, where n may be very large if a continuously variable spectrum was emitted). Matrix solver 42 solves the n numbers in absorbance registers 37 for simultaneous solution of up to n qualitative concentrations, by solving n equations with n unknowns, and the results are stored in qualitative registers 47 (consisting of n registers 47a, 47b, ... 47n). Concentration adjuster 49 corrects the numbers in qualitative registers 47, producing concentration-based results, which are then stored in quantitative registers 51 (consisting of n registers 51a, 51b, ... 51n). Adjuster 49 uses constants stored in conversion factor register 53 in order to perform accurate conversions. The values in register 53 may be either factory programmed, determined by calibration trials, determined from previous measurements, user-entered, or otherwise modified. The final concentration-based results stored in quantitative registers 51 are displayed on output device 55.

OPERATION OF THE DEVICE

The operation of a device so constructed may now be described in detail. In the following example, the wavelengths suggested are merely illustrative, and are not intended to represent the best possible, or even adequate, wavelengths for the functions described. In this example, the concentration of bilirubin will be calculated from light of three wavelengths emitted into, and detected back from, a human finger. Therefore, n (the number of wavelengths used) equals 3. The concentration calculated is the concentration of bilirubin in the arterial blood. Concentrations are not calculated from the absorbance of water, as this concentration is assumed to be nearly constant in this example. Nor is a concentration calculated from the third relative absorbance calculated, which represents the residual variation from each pulse unaccounted for by bilirubin or by water. This third component thus represents an error of the measurement due to unaccounted-for, but measured, substances.

In this example, the wavelength emitted by source 11a is selected such that bilirubin concentration affects absorbance greatly, while the absorbance of wavelength a by water is not significant. One such wavelength is near 470 nm, but other appropriate wavelengths may be used, alone or in combination. The wavelength emitted by source 11b is selected such that water concentration affects absorbance greatly, while the absorbance by bilirubin is less significant. Such wavelengths may reside in the infrared range, near or above 1200 nm. A third wavelength, emitted by source 11n, is chosen that is affected both by water and by bilirubin, possibly in the 900-1200 nm range.

The emitter and detector are placed on opposite sides of a human adult finger, and the device is turned on. Other detector/emitter configurations are also possible. In the first stage of operation, analog waveform information is obtained and converted to numeric values. FIG. 2 shows various sample waveforms obtained. First, signal 107 is obtained from detector 17. The DC component is removed by filter 21, leaving filtered signal 111. Filtered signal 111 is amplified by amplifier 27, producing amplified signal 114. Demodulator 31 separates each of the component signals in signal 114 into signals corresponding to the detected intensity of each emitted wavelength. In this example, signal 121a corresponds to the detected intensity of light produced by emitter 11a, while signal 121b corresponds to the detected intensity of light produced by emitter 11b, and signal 121n corresponds to the detected intensity of light produced by emitter 11n. Peak signal detector 33 follows the average peak value for each component signal, producing peak absorbance signals 125a, 125b, and 125n. These peak absorbance signals represent the pulsatile changes in absorbance due to the changes with each pulse in the amount of blood between emitter 11 and detector 17. However, these pulsatile changes are merely qualitative, in that they represent increases and decreases in the amount of chromophore between emitter 11 and detector 17, but not absolute amounts in the bloodstream. Now that all analog signals have been processed, the conversion of the pulsatile changes in amount to quantitative concentration based results can begin. From this point on, processing is numeric, rather than analog. Of course, the processing of the analog signals could have occurred in a different order, with similar results, provided that the final result represents a qualitative change in the some pulsatile feature of the detected radiation.

Figure 3:
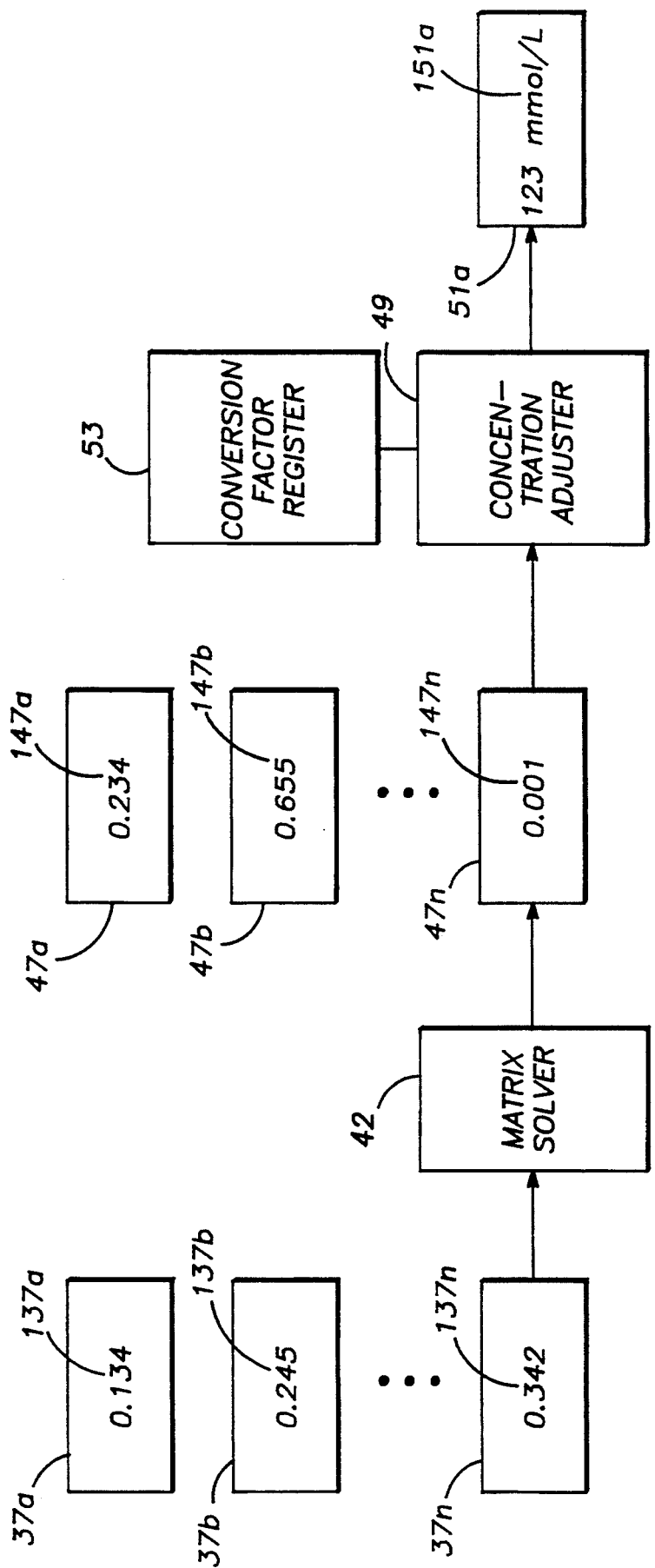

FIG. 3 illustrates the processing of the numeric values. Signals from A-to-D convertor 35 are stored as peak absorbance values 137a, 137b, and 137n in absorbance registers 37a, 37b, and 37n, respectively. These values reflect the peak absorbance at each wavelength, but not concentration. In order to solve for the relative concentrations of each of the chromophores, matrix solver 42 performs a matrix solution of 3 equations with 3 unknowns, and stores qualitative bilirubin value 147a, qualitative water value 147b, and qualitative unknown value 147n in registers 47a, 47b, and 47n, respectively. These qualitative chromophore values reflect the relative contribution of each of the chromophores to the total absorbance. The unknown value corresponds to the changes in absorbance at the three wavelengths not explained by bilirubin and water. Note that in the example in FIG. 3 that qualitative bilirubin value 147a is smaller than qualitative water value 147b, reflecting the dilution of small amounts of bilirubin in large amounts of water, and also that qualitative unknown value 147n is quite small, reflecting the use of wavelengths at which only a small amount in the total variation in absorbance is unexplained by variations in the concentration of water and bilurubing. In practice, the concentration of certain other absorbers (such as hemoglobin) may need to accounted for in order to achieve a similarly good fit.

At this time, concentration adjuster 49 multiplies the values stored in qualitative registers 47 by factory programmed values stored in conversion factor register 53, to produce concentration based results, which are stored in result registers 51a, 51b, and 51n. In this case, the relative amount of bilirubin is divided by the relative amount of water, and multiplied by an estimate of the concentration of water in the blood, to produce quantitative bilirubin concentration 151a. The concentration of water and the concentration of the unknown substances are not calculated in this embodiment. The bilirubin blood concentration is displayed on output 55.

The device as described may need to be calibrated, such that the conversion factors in register 53 are entered by the user. For example, if the device measures a relative bilirubin concentration of 1, while a near-simultaneous blood sample measured by a different method shows a bilirubin concentration of 10, then future qualitative concentrations will need to be multiplied by 10 in order to be expressed as absolute bloodstream concentration. Furthermore, the absolute concentration of water would not always need to be measured in order to determine a concentration. Once the conversion factors had been adjusted properly, the concentration determined from the conversion factor would only need to be corrected for changes in pulse volume. That is, if the pulse volume is twice as large, then measured absorbance changes in bilirubin reflect the chromophore in twice as much blood volume, and the changes in absorbance would be twice as large as well. In order to prevent an error in calculation of concentration, one may need to correct for the size of the pulse. It is possible to judge pulse size by measuring the pulsatile changes in absorbance of a stable reference chromophore, such as water. If the change in water absorbance is twice as large, then the bilirubin absorbance change should be cut by half when determining concentration. Water concentration may be measured due to the high absorbance by water of wavelengths above 1000 nm, particularly those above 1200 nm.

This calculation sequence repeats indefinitely until the device is turned off, and the bilirubin value on the display is updated each pulse, and may represent a running average of more than one of the most recent calculated values.

The wavelengths of the device so constructed may be adjusted to yield the concentration of substances such a glucose, ketones, metabolic products, hemoglobin, or medications. In theory, use of many wavelengths or use of a continuous spectrum of emitted light could allow for solution of a large number of blood components, many with high accuracy not previously possible using a noninvasive device. Furthermore, if the concentration of a substance, with that substance changing color in response to pH, is measured (the two components being the different colored forms of the dye), then the concentration related result could even be the pH of the blood.

A device so constructed would be portable, inexpensive, and allow measurement of blood components that, up to now, has required blood sampling. In addition, as the measurement is continuous, monitoring of substances such as glucose, that now needs to be performed quite frequently on ill patients, can be done without the loss of large volumes of blood. In fact, in premature infants tests are often skipped due to the small total blood volume in these infants (sometimes as small as 3 tablespoons), and a noninvasive device such as this may allow measurement of substances now not measured even though medically important. Such a device meets well the three requirements specified earlier: 1) that it measure accurately through human tissue, and 2) that it measure the concentration in the blood, and not the concentration in other tissues, and 3) that it measure a concentration, not just a unitless percentage. Such a device would have immediate medical applications.

I claim:

1. A spectrophotometer for noninvasively determining the concentration of a first optically absorptive substance within the blood of a patient, comprising:
   means for emitting first and second wavelengths of light into a selected tissue of said patient;
   means for detecting a first intensity of portions of said first wavelength of light passing through said selected tissue and a second intensity of said second wavelength passing through said selected tissue, said first and second intensities each being related to interaction of said first and second wavelengths of light with a plurality of substances within the blood of said patient, said plurality of substances including said first absorptive substance;

means for measuring a first pulsatile feature of said first detected intensity and a second pulsatile feature of said second detected intensity, said first and second pulsatile features each being related to changes over time in the volume of the blood within said selected tissue; and means for estimating concentration of said first substance within the blood of said patient based on said first and second measured pulsatile features.

2. The spectrophotometer of claim 1 wherein said means for measuring includes means for filtering constant intensity components from said first and second detected intensities.

3. The spectrophotometer of claim 1 wherein said first and second pulsatile features correspond to changes in at least one of the characteristics of said substances selected from the set consisting of: absorbance, scattering, transmission, turbidity, coherence, and optical rotation.

4. The spectrophotometer of claim 1 wherein said interaction corresponds to absorbance of said transmitted light by said first substance, and wherein said means for measuring includes means for measuring changes in absorbance of said first and second wavelengths of light by said first substance.

5. The spectrophotometer of claim 1 wherein said means for estimating includes means for solving a set of simultaneous equations relating said first and second measured pulsatile features to relative concentrations of said first substance.

6. The spectrophotometer of claim 1 wherein said means for estimating concentration includes means for estimating concentration of said first substance within arterial blood of said patient.

7. The spectrophotometer of claim 1 wherein said means for estimating concentration includes means for estimating concentration of said first substance within venous blood of said patient.

8. A spectrophotometer for noninvasively determining the concentration of a first optically absorptive substance within the blood of a patient, comprising:

means for transmitting first and second wavelengths of light through a selected tissue of said patient;

means for detecting the intensities of portions of said first and second wavelengths of light passing through said selected tissue, said intensities being related to interaction of said transmitted light with said first substance and with a reference substance within the blood of said patient, said reference substance comprising water;

means for measuring at least one pulsatile feature of said detected intensities, said pulsatile features being induced by changes in the amounts of said absorptive substances within the blood of said patient; and means for estimating concentration of said first substance within the blood of said patient based on said measured pulsatile features, said means for estimating including means for computing the ratio of said relative concentration of said first substance to said relative concentration of said reference substance; and means for adjusting said ratio of said relative concentration in accordance with a calibration factor in order to produce an adjusted ratio;

whereby said adjusted ratio corresponds to absolute concentration of said first substance within the blood of said patient.

9. The spectrophotometer of claim 8 wherein said first substance is selected from the group consisting of: hemoglobin, bilirubin, glucose, ketones, cholesterol, medications, toxins, and products of human metabolism.

10. A method for noninvasively determining the concentration of a first optically absorptive substance within the blood of a patient, comprising the steps of:

emitting first and second wavelengths of light into a selected tissue of said patient;

detecting a first intensity of portions of said first wavelength of light passing through said selected tissue and a second intensity of said second wavelength passing through said selected tissue, said first and second intensities each being related to interaction of said first and second wavelengths of light with a plurality of substances within the blood of said patient, said plurality of substances including said first absorptive substance;

measuring a first pulsatile feature of said first detected intensity and a second pulsatile feature of said second detected intensity, said first and second pulsatile features each being related to changes over time in the volume of the blood within said selected tissue; and estimating concentration of said first substance within the blood of said patient based on said first and second measured pulsatile features.

11. The method of claim 10 wherein said step of measuring includes the step of filtering constant intensity components from said first and second detected intensities.

12. The method of claim 10 wherein said first and second pulsatile features correspond to changes in at least one of the characteristics of said substances selected from the set consisting of: absorbance, scattering, transmission, turbidity, coherence, and optical rotation.

13. The method of claim 12 wherein said interaction corresponds to absorbance of said transmitted light by said first and reference substances, and wherein said step of measuring includes the step of measuring changes in absorbance of said transmitted light by said substances.

14. The method of claim 10 wherein said step of estimating includes the step of solving a set of simultaneous equations relating said first and second pulsatile features to relative concentrations of said first substance.

15. The method of claim 10 wherein said step of measuring said first and second pulsatile features includes the steps of:

measuring a qualitative pulsatile change in the amount of blood within said selected tissue, said pulsatile change being related to the amount of a reference substance in the blood of said patient, said first and second wavelengths of light encountering said reference substance during propagation through said selected tissue, said change occurring proximate a predefined calibration time.

determining an actual concentration of said reference substance in the blood of said patient at a time proximate said calibration time by an independent standard method;

calculating a conversion factor relating said qualitative pulsatile change to said actual concentration; and converting subsequent pulsatile changes in the amount of said reference substance in the blood to concentrations of said reference substance in the blood in accordance with said conversion factor.

16. The method of claim 15 further including the step of injecting said reference substance into the blood of said patient.

17. A method for noninvasively determining the concentration of a first optically absorptive substance within the blood of a patient, comprising the steps of:

transmitting first and second wavelengths of light through a selected tissue of said patient;

detecting the intensities of portions of said first and second wavelengths of light passing through said selected tissue, said intensities being related to interaction of said transmitted light with said first substance and with a reference substance within the blood of said patient wherein said interaction corresponds to absorbance of said transmitted light by said first and reference substances, and wherein said step of measuring includes the step of measuring changes in absorbance of said transmitted light by said substances, said reference substance comprising water;

measuring at least one pulsatile feature of each of said detected intensities, said pulsatile features being related to changes in the amounts said absorptive substances within the blood of said patient wherein said at least one pulsatile feature corresponds to changes in at least one of the characteristics of said substances selected from the set consisting of: absorbance, scattering, transmission, turbidity, coherence, and optical rotation, said step of measuring including the step of filtering constant intensity components from said detected intensities: and estimating concentration of said first substance within the blood of said patient based on said measured pulsatile features, said step of estimating including the steps of;

solving a set of simultaneous equations relating said at least one pulsatile feature to relative concentrations of said first and reference substances;

computing the ratio of said relative concentration of said first substance to said relative concentration of said reference substance; and adjusting said relative concentration ratio in accordance with a calibration factor;

whereby said adjusted ratio corresponds to absolute concentration of said first substance within the blood of said patient.

18. A method for noninvasively determining the concentration of a first optically absorptive substance within the blood of a patient, comprising the steps of;

transmitting first and second wavelengths of light through a selected tissue of said patient;

detecting the intensities of portions of said first and second wavelengths of light passing through said selected tissue, said intensities being related to interaction of said transmitted light with said first substance and with a reference substance within the blood of said patient wherein said reference substance exhibits a time-invariant concentration;

measuring at least one pulsatile feature of each of said detected intensities, said pulsatile features being related to changes in the amounts said absorptive substances within the blood of said patient, said step of measuring said at least one pulsatile feature including the steps of:

estimating a pulsatile change in the amount of blood within said selected tissue, said pulsatile change being related to the amount of said reference substance within the blood of said patient proximate a first calibration time;

estimating a pulsatile change in the amount of said reference substance within the blood of said patient proximate a second calibration time;

calculating a pulse volume ratio by comparing said estimated pulsatile changes occurring at said first and second calibration times; and correcting measured pulsatile changes in the amount of said first substance made proximate to said second calibration time in accordance with said pulse volume ratio; and, estimating concentration of said first substance within the blood of said patient based on said measured pulsatile features.

19. A method for noninvasively determining the concentration of at least one optically absorptive substance within the blood of a patient, comprising the steps of:

transmitting a plurality of wavelengths of light through a selected tissue of said patient;

detecting the respective intensities of portions of said plurality of wavelengths of light passing through said selected tissue, at least one of said wavelengths of light being selected to be at least partially absorbed by water;

measuring a pulsatile feature of each of said detected intensities, said pulsatile feature of each of said detected intensities being related to changes in the amount of said at least one said optically absorptive substance within the blood of said patient; and estimating concentration of said at least one said optically absorptive substance within the blood of said patient based on said measured pulsatile features, said step of estimating including the step of calculating a relative amount of water within the blood of said patient based on said measured pulsatile feature of said at least one wavelength of light at least partially absorbed by water.

20. A spectrophotometer for noninvasively determining the concentration of a first optically absorptive substance within the blood of a patient, comprising:

means for emitting first and second wavelengths of light substantially simultaneously into a selected volume of tissue of said patient;

means for detecting the intensities of portions of said first and second wavelengths of light passing through said selected volume of tissue, said intensities being related to interaction of said transmitted light with said first substance and with a reference substance within the blood of said patient;

means for measuring at least one pulsatile feature of each of said detected intensities, said pulsatile features being induced by changes in the volume of blood within said selected volume of tissue wherein said pulsatile features are related to concentration of said absorptive substance within the blood of said patient; and means for estimating concentration of said first substance within the blood of said patient based on said measured pulsatile features.

* * * * *

UNITED STATES PATENT AND TRADEMARK OFFICE
CERTIFICATE OF CORRECTION

PATENT NO. : 5,337,745

DATED : August 16, 1994

INVENTOR(S) : David A. Benaron

It is certified that error appears in the above-identified patent and that said Letters Patent is hereby corrected as shown below:

Abstract, line 10, after "bloodstream" delete "is".

Column 1, line 12, change "on" to --to--.

Column 2, line 2, change "thus" to --Thus--.

Column 4, line 49, after "length" change "a" to --11a--.

Signed and Sealed this

Twenty-first Day of March, 1995

*Attest:*

BRUCE LEHMAN

*Attesting Officer*     *Commissioner of Patents and Trademarks*